(12) United States Patent
Anderson et al.

(10) Patent No.: US 12,280,263 B2
(45) Date of Patent: Apr. 22, 2025

(54) LEADLESS CARDIAC PACEMAKER DEVICE CONFIGURED TO PROVIDE HIS BUNDLE PACING

(71) Applicant: BIOTRONIK SE & CO. KG, Berlin (DE)

(72) Inventors: Nicholas R. Anderson, Beaverton, OR (US); Jeffrey A. Von Arx, Lake Oswego, OR (US); Hannes Kraetschmer, West Linn, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 18/302,914

(22) Filed: Apr. 19, 2023

(65) Prior Publication Data

US 2023/0248984 A1 Aug. 10, 2023

Related U.S. Application Data

(62) Division of application No. 16/820,787, filed on Mar. 17, 2020, now Pat. No. 11,660,457.

(Continued)

(51) Int. Cl.
*A61N 1/37* (2006.01)
*A61B 17/34* (2006.01)
(Continued)

(52) U.S. Cl.
CPC ........ *A61N 1/3756* (2013.01); *A61B 17/3468* (2013.01); *A61N 1/056* (2013.01); *A61N 1/3702* (2013.01); *A61N 1/3706* (2013.01); *A61N 1/37211* (2013.01); *A61N 1/37512* (2017.08); *A61N 1/37518* (2017.08); *A61B 5/287* (2021.01); *A61B 5/341* (2021.01); *A61B 2017/00044* (2013.01); *A61B 2017/00292* (2013.01)

(58) Field of Classification Search
CPC .......................... A61N 1/3756; A61N 1/37518
See application file for complete search history.

(56) References Cited

U.S. PATENT DOCUMENTS 7,996,087 B2 8/2011 Cowan et al.
8,068,920 B2 * 11/2011 Gaudiani ............... A61B 6/485
607/122

(Continued)

FOREIGN PATENT DOCUMENTS

WO 2008011626 A1 1/2008
WO 2009128809 A1 10/2009

*Primary Examiner* — Eric D. Bertram
(74) *Attorney, Agent, or Firm* — Laurence A. Greenberg; Werner H. Stemer; Ralph E. Locher

(57) ABSTRACT

A leadless cardiac pacemaker device is configured to provide HIS bundle pacing and contains a housing having a tip, a first electrode arranged on the housing in the vicinity of the tip, the first electrode being configured to engage with intra-cardiac tissue, and a second electrode arranged on the housing at a distance from the tip of the housing. A processor is enclosed in the housing and operatively connected to the first electrode and the second electrode. The processor is configured to process a reception signal received by at least one of the first electrode and the second electrode and to generate a pacing signal to be emitted using at least one of the first electrode and the second electrode.

6 Claims, 7 Drawing Sheets

Related U.S. Application Data

(60) Provisional application No. 62/837,740, filed on Apr. 24, 2019.

(51) Int. Cl.
*A61N 1/05* (2006.01)
*A61N 1/372* (2006.01)
*A61N 1/375* (2006.01)
A61B 5/287 (2021.01)
A61B 5/341 (2021.01)
A61B 17/00 (2006.01)

(56) References Cited

U.S. PATENT DOCUMENTS

| | | | |
|---|---|---|---|
| 8,078,287 B2 | 12/2011 | Liu et al. | |
| 8,634,935 B2 * | 1/2014 | Gaudiani | A61B 8/5292 607/116 |
| 8,700,181 B2 * | 4/2014 | Bornzin | A61N 1/3684 607/9 |
| 8,996,109 B2 | 3/2015 | Karst et al. | |
| 9,265,938 B2 * | 2/2016 | Gaudiani | A61B 6/481 |
| 9,610,438 B2 | 4/2017 | Schilling | |
| 9,662,487 B2 | 5/2017 | Kveen et al. | |
| 10,758,724 B2 | 9/2020 | Koop | A61N 1/372 |
| 11,577,075 B1 * | 2/2023 | Gaudiani | A61B 6/481 |
| 11,648,397 B1 * | 5/2023 | Gaudiani | A61B 6/504 600/424 |
| 11,660,457 B2 * | 5/2023 | Anderson | A61N 1/3706 606/129 |
| 2008/0082136 A1 * | 4/2008 | Gaudiani | A61B 6/481 607/9 |
| 2009/0259272 A1 | 10/2009 | Reddy | A61N 1/0573 607/9 |
| 2011/0160801 A1 | 6/2011 | Markowitz | A61N 1/37217 607/60 |
| 2012/0041530 A1 * | 2/2012 | Gaudiani | A61B 8/5292 607/122 |
| 2012/0158111 A1 * | 6/2012 | Khairkhahan | A61N 1/37512 607/127 |
| 2013/0116738 A1 * | 5/2013 | Samade | A61N 1/3684 607/9 |
| 2013/0123872 A1 * | 5/2013 | Bornzin | A61N 1/3684 607/17 |
| 2013/0324825 A1 | 12/2013 | Ostroff et al. | |
| 2014/0107723 A1 * | 4/2014 | Hou | A61N 1/3756 607/9 |
| 2014/0257101 A1 * | 9/2014 | Gaudiani | A61B 6/485 600/407 |
| 2014/0257324 A1 * | 9/2014 | Fain | A61N 1/3756 606/129 |
| 2016/0008612 A1 * | 1/2016 | Régnier | A61N 1/37282 607/32 |
| 2016/0193459 A1 * | 7/2016 | Gaudiani | A61B 6/481 607/122 |
| 2016/0228712 A1 * | 8/2016 | Koop | A61N 1/368 |
| 2016/0279423 A1 * | 9/2016 | Kelly | A61M 25/0136 |
| 2018/0132754 A1 | 5/2018 | Kusumoto | A61B 5/287 |
| 2018/0264274 A1 * | 9/2018 | Haasl | A61N 1/059 |
| 2019/0083800 A1 * | 3/2019 | Yang | A61N 1/0573 |
| 2019/0083801 A1 * | 3/2019 | Yang | A61N 1/37518 |
| 2019/0111265 A1 | 4/2019 | Zhou | A61B 5/349 |
| 2019/0126040 A1 | 5/2019 | Shuros et al. | |
| 2019/0134412 A1 | 5/2019 | Shuros | A61N 1/3756 |
| 2019/0134413 A1 * | 5/2019 | Mar | A61N 1/375 |
| 2020/0101279 A1 * | 4/2020 | Drake | A61N 1/37205 |

* cited by examiner

| Previous Sensed V | Current Sensed A | Previously Sensed V | Pacemaker Action |
|---|---|---|---|
| Normal | Normal | Normal | Output at nominal |
| Normal | None | Intrinsic (morphology) | Lower atrial threshold and gauge timing based on intrinsic beat, pace earlier than intrinsic V/V of previously cycle by some value (e.g. 10% or 10 ms) |
| Normal | Farfield verification only | Normal | Lower atrial threshold, possibly shorten blanking period |
| None | Normal | Normal | No change |
| Normal | Low | Normal | Lower atrial threshold |
| Normal | None | PVC (morphology) | Lower atrial threshold, shorten blanking period |

FIG. 15

| Previous Sensed V | Sensed A | Current Sensed V | Pacemaker Action |
|---|---|---|---|
| Normal | Normal | Normal | Output at nominal value |
| None | Normal | N/A | Output at safety value |
| Normal | Normal | None | Output at safety value on next cycle |
| Normal | None (timeout) | N/A | Output at nominal value |
| Normal | Normal | Fusion | Shorten in A/V |
| Normal | Normal | Intrinsic | Shorten in A/V (HIS bundle pacing is attempting to synch L and R Ventr) |
| Normal | None | PVC (morphology) | Possible outcomes, shorten A/V, pace at nominal intervals for a short period of time, wait for intrinsic atrial activity / increase rate for a short period of time to encourage BiV capture |
| Normal | Normal | QRS indicates capture of HIS bundle and ventricular muscle | Lower output to attempt HIS only capture on next cycle |

LEADLESS CARDIAC PACEMAKER DEVICE CONFIGURED TO PROVIDE HIS BUNDLE PACING

CROSS-REFERENCE TO RELATED APPLICATION

This application is a Divisional of co-pending U.S. patent application Ser. No. 16/820,787, filed on Mar. 17, 2020, now U.S. Pat. No. 11,660,457, which claims the benefit, under 35 U.S.C. § 119(e), of provisional patent application No. 62/837,740 filed Apr. 24, 2019; the prior applications are herewith incorporated by reference in their entireties.

BACKGROUND OF THE INVENTION

Field of the Invention

The instant invention generally relates to a leadless cardiac pacemaker device and to a delivery system for the placement of a leadless pacemaker device in a human heart. The instant invention also relates to a method for placing a leadless pacemaker device using a delivery system.

In recent years, leadless pacemakers have received increasing attention. Leadless pacemakers, in contrast to pacemakers implanted subcutaneously using leads extending transvenously into the heart, avoid leads in that the pacemaker device itself is implanted into the heart, the pacemaker having the shape of a capsule for implantation into cardiac tissue, in particular the right ventricular wall of the right ventricle. Such leadless pacemakers exhibit the inherent advantage of not using leads, which can reduce risks for the patient involved with leads transvenously accessing the heart, such as the risk of pneumothorax, lead dislodgement, lead endocarditis, cardiac perforation, venous thrombosis and the like.

Leadless pacemakers are currently configured for implantation in the right ventricle and during implant are placed in or on the right ventricular wall. As such leadless pacemakers primarily cause a pacing of the right ventricle, drawbacks coming with existing leadless pacemakers may include a reduction in the right ventricular filling volume, a lack of the so-called A to V synchrony (relating to the proper sequence of atrial and ventricular contractions), a potentially excessive right ventricular pacing (which cannot be minimized due to the placement of the leadless pacemaker in the right ventricle), and a lack of left ventricular (LV) to right ventricular (RV) synchrony.

Approaches exist to provide for a so-called HIS bundle pacing in order to synchronously pace both the right ventricle and the left ventricle by injecting a stimulus via the HIS bundle. Current pacemaker devices for HIS bundle pacing, as known for example from U.S. Pat. Nos. 8,565,880 and 8,078,287, however use leads extending from the pacemaker device transvenously into the heart to excess the HIS bundle.

U.S. Pat. No. 8,078,287 herein describes a mapping technique for placing a lead in the right ventricle by monitoring cardiac signals to obtain electrograms including so-called A, V, and H waves, A waves corresponding to the right atrial depolarization sensed by a mapping electrode, V waves corresponding to the right ventricular depolarization sensed by a mapping electrode, and H waves corresponding to events indicative of A/V conduction of electrical impulses as recorded by a mapping electrode.

SUMMARY OF THE INVENTION

There is a desire to provide a pacemaker device which may exhibit the advantages of a leadless pacemaker, while avoiding drawbacks such as a lack of A to V synchrony and left ventricular (LV) to right ventricular (RV) synchrony as inherent with right ventricular pacing.

There in addition is a desire to provide a delivery system allowing for an easy and fast, yet reliable placement of a pacemaker device.

Such desires are addressed by a leadless cardiac pacemaker device configured to provide HIS bundle pacing.

A leadless pacemaker device, a delivery system and a method for placing a leadless pacemaker device according are provided as independent claims. Further embodiments are subject matter of dependent claims.

In one aspect, the pacemaker device comprises a housing having a tip. A first electrode is arranged on the housing in the vicinity of the tip. The first electrode is configured to engage with intra-cardiac tissue. A second electrode is arranged on the housing at a distance from the tip of the housing. A processor is enclosed in the housing and operatively connected to the first electrode and the second electrode. The processor is configured to process a reception signal received by at least one of the first electrode and the second electrode and to generate a pacing signal to be admitted using at least one of the first electrode and the second electrode.

It hence is proposed to use a leadless cardiac pacemaker device to provide HIS bundle pacing. By providing a pacing at the HIS bundle, drawbacks associated with current leadless pacemakers can be avoided, for example allowing to avoid a reduction in the right ventricular filling volume, to improve the atrial to ventricular (A/V) synchrony, to avoid a predominant right ventricular pacing, and to improve the left ventricular (LV) to right ventricular (RV) synchrony. In particular, by pacing at the HIS bundle, the intrinsic conductive system of the heart is used, providing for a synchronous stimulation of the right ventricle and the left ventricle via the intrinsic right bundle branch and left bundle branch extending from the HIS bundle to extend about the right ventricle respectively the left ventricle. Hence, a synchronous pacing for both the right ventricle and the left ventricle is provided, avoiding an asynchronous and asymmetric pacing of the ventricles.

The housing provides for an encapsulation of the leadless pacemaker device, the leadless pacemaker device including all required components for autarkic operation, such as a processor, an energy storage such as a battery, electric and electronic circuitry and the like, within the housing. The processor may be any kind of control logic such as a microprocessor, a microcontroller, or one or more finite state machine(s). A finite state machine uses less power than a microprocessor but has less flexibility and less programmability. The housing is fluid-tight such that the leadless pacemaker device may be implanted into the heart and may be kept close to cardiac tissue over an extended period of time to provide for a long-time, continuous cardiac pacing operation.

The leadless pacemaker device, in one aspect, is to be placed in the right atrium. The pacemaker device hence is not placed in the right ventricle, but on an atrial wall, which makes it necessary to provide an adapted fixation for the pacemaker device by fixing it to the atrial wall.

In one aspect, the leadless pacemaker device comprises a fixation device having at least one fixation element arranged at the tip of the housing for fixing the pacemaker device to intra-cardiac tissue, in particular the atrial wall. In one embodiment, one or multiple fixation elements in the shape of thin wires, for example nitinol tines exhibiting a shape memory effect, may be provided, such wires for example having a curvature comprising a small radius, for example smaller than 1.5 mm and hence exhibiting a rather tight curvature in order to minimize the chance that such fixation elements penetrate the atrial wall. In another embodiment, a fixation element in the shape of a screw anchor may be provided, such screw anchor allowing to screw the leadless pacemaker device into the atrial wall and having a rather small diameter, for example smaller than 2 mm.

The fixation device at the tip of the housing of the leadless pacemaker device allows to place the leadless pacemaker device on the atrial wall and to fix the leadless pacemaker device via the fixation device to the atrial wall, such that the leadless pacemaker device upon implantation is fixedly held and permanently placed within cardiac tissue.

In one aspect, the first electrode arranged in the vicinity of the tip of the housing is located on a pin fixed to the housing, the pin serving to engage with cardiac tissue when implanting the leadless pacemaker device. The pin has a pointed shape and is inserted into cardiac tissue, in particular the atrial wall in the vicinity of the HIS bundle, such that the first electrode placed on the tip comes to rest at a location close to the HIS bundle for injecting a stimulating signal towards the HIS bundle for HIS bundle pacing.

The pin may for example have a length between 1 mm and 2 mm, for example approximately 1.5 mm.

In another embodiment, the first electrode may be placed on a screw anchor serving as a fixation element for the fixation device. Such a screw anchor is inserted into cardiac tissue, in particular the atrial wall, when placing the leadless pacemaker device in the heart. The first electrode arranged on the screw anchor in this way comes to rest at a location close to the HIS bundle for providing for an effective HIS bundle pacing.

The pin or the screw anchor may carry a coating for (partial) insulation such that only the first electrode placed on the pin respectively the screw anchor is exposed. This may allow minimizing a risk of accidental atrial capture. The insulating coating can be paralyne, PTFE (PTFE—Polytetrafluoroethylene), silicone, a silicone polymer, polyurethane, polyimide, or some other biocompatible coating.

In one aspect, the leadless pacemaker device comprises a multiplicity of first electrodes arranged on the housing in the vicinity of the tip. For example, multiple pins may be provided at the tip of the housing (e.g. two or three pins), each pin carrying a first electrode. Alternatively, a screw anchor device having multiple arms to form a double or triple helix or the like may be provided, each arm carrying a first electrode.

The processor herein, in one embodiment, may be configured to select at least one of the multiplicity of the first electrodes for operation, for example for receiving a reception signal and/or for emitting a pacing signal. By selecting a proper first electrode located particularly close to the HIS bundle, an effective HIS bundle pacing may be achieved. Because multiple first electrodes are present, the selection of a suitable first electrode allows to easily and effectively stimulate the HIS bundle without having to reposition the leadless pacemaker.

In one aspect, the second electrode is formed by an electrode ring circumferentially extending about the housing. Alternatively, the second electrode may for example be formed by a patch or another electrically conductive area formed on the housing. The second electrode is placed at a distance from the tip of the housing and hence at a distance from the first electrode arranged in the vicinity of the tip.

In one embodiment with a multiplicity of first electrodes, two or more of the multiplicity of the first electrodes can be selected to pace differentially between. This allows for an even larger number of pacing vectors than always using the second electrode as the pacing return. This helps to maximize the chance that the device can be programmed to stimulate the HIS bundle without repositioning. The cost of this approach may be longevity, since higher pacing voltages will likely be needed since the first electrodes may have higher impedance than the (large) second electrode.

One challenge in the context of implanting a leadless pacemaker for HIS bundle pacing is detecting the HIS bundle in order to place the leadless pacemaker in close proximity to the HIS bundle for effective pacing. In one embodiment, the processor of the leadless pacemaker device is configured to process, as a reception signal in a mapping mode during placement of the pacemaker device in a human heart, a first signal vector sensed between the first electrode and the second electrode. The leadless pacemaker device, by means of the first signal vector, hence may take up an electrogram in real-time, the electrogram being indicative of electrical activity at or close to the HIS bundle. Because the first electrode and the second electrode may also be used for the pacing to emit a pacing signal towards the HIS bundle for stimulation, the signal vector picked up by means of the first electrode and the second electrode during placement resembles what the leadless pacemaker device will see during actual operation after implant, because the same electrodes are used for mapping and for pacing after implant. A strong signal reception during placement hence is indicative of an effective energy injection for pacing after implant.

In one embodiment, the leadless pacemaker device comprises a communication interface for transmitting, in the mapping mode, a communication signal comprising information relating to the first signal vector from the pacemaker device to an external device outside of the human body, for example in the shape of a programmer wand. The communication interface serves to contactlessly (wirelessly) transmit communication signals from the leadless pacemaker device towards the external device, information hence being transmitted from the leadless pacemaker device to the external device using telemetry. In this way, a real-time electrogram picked up by the first electrode and the second electrode may be transmitted to the external device, such that the electrogram may be monitored for achieving a mapping in order to access the HIS bundle by the leadless pacemaker device. In one embodiment the real-time electrogram can also be programmed to be between any two first electrodes, or between multiple first electrodes electrically tied together and the second electrode. The different allowed sensing vectors allow the implanter to search a bit electronically for a HIS signal without necessarily having to physically reposition the electrodes.

The communication interface may for example be configured to transmit communication signals using an inductive coupling, MICS (medical implant communication service), BLE (Bluetooth low energy), acoustic communication, or E-field communication.

In one embodiment, the leadless pacemaker device comprises a third electrode arranged on the housing. The third electrode herein may for example be placed at a far end of the housing opposite the tip. The third electrode is operatively connected to the processor, such that the processor is enabled to receive and process signals received via the third electrode.

In one aspect, the processor is configured to process, as a reception signal, at least one of a second signal vector sensed between the first electrode and the third electrode and a third signal vector sensed between the second electrode and the third electrode.

The second signal vector arising between the first electrode and the third electrode herein may also be referred to as farfield vector, the first electrode and the third electrode exhibiting a distance with respect to each other larger than the second electrode and the third electrode. The second signal vector may in particular be indicative of ventricular contractions, such that by means of the second signal vector an evoked response after injecting a pacing stimulus may be captured.

The third signal vector sensed between the second electrode and the third electrode may be used to sense atrial contractions in order to provide for an atrial to ventricular synchronization by timely injecting a stimulus at the HIS bundle following atrial contractions. The third signal vector may alternatively or in addition also be used to sense ventricular contractions, in response to an HIS bundle pacing stimulus, wherein in this case atrial contractions need to be filtered out of the third signal vector.

In one aspect, the same set (or sub-set) of electrodes of the leadless pacemaker device is used both for sensing contraction signals as well as for emitting pacing stimulation signals. For this, in one embodiment, the processor of the leadless pacemaker device is configured to switch between a sensing mode and a stimulus mode by alternating between the processing of received signals and the generation of pacing signals. In particular, the processor may be configured to, in a first phase of the cardiac cycle, sense for atrial contractions. If atrial contractions are captured, the processor may switch to a stimulus mode in which a pacing signal is generated and emitted using at least one of the first electrode and the second electrode in a second phase of the cardiac cycle. After the pacing signal has been emitted, the processor switches back to a sensing mode to now sense ventricular contractions which are evoked as a response to the pacing stimulus, the ventricular contractions for example being picked up by the second signal vector sensed between the first electrode and the third electrode in a third phase of the cardiac cycle. Following the sensing of ventricular contractions, atrial contractions may be sensed anew to continue pacing operation.

In another aspect, a delivery system for placement of a leadless pacemaker device in a human heart is provided. The delivery system comprises: a catheter device for insertion into the human body, the catheter device comprising a lumen and a distal end to be inserted into the human body; and a leadless pacemaker device configured to provide HIS bundle pacing. The pacemaker device is received within the lumen in the vicinity of the distal end of the catheter device. A first mapping electrode and a second mapping electrode are arranged in the vicinity of the distal end of the catheter device for sensing, in a mapping mode, a mapping signal vector in between the first mapping electrode and the second mapping electrode, the mapping signal vector representing an electrogram of cardiac activity.

The delivery system serves to place the leadless pacemaker device in the human heart such that the leadless pacemaker device comes to rest for example in the right atrium in close proximity to the HIS bundle. The delivery system herein provides for a mapping such that during placement of the leadless pacemaker device it may be observed whether the leadless pacemaker device has reached the HIS bundle and hence has obtained its correct position within e.g. the atrium.

To provide for a mapping, the delivery system comprises a first mapping electrode and a second mapping electrode. The first mapping electrode and the second mapping electrode serve to pick up a mapping signal vector, the mapping signal vector representing an electrogram of cardiac activity, for example an HIS bundle electrogram picked up at the HIS bundle and suitable to assess whether the HIS bundle has suitably been approached.

Different arrangements of the first mapping electrode and the second mapping electrode are conceivable.

In one embodiment, the pacemaker device comprises a housing having a tip, the first mapping electrode being arranged on the housing in the vicinity of the tip, the second mapping electrode being arranged on the housing at a distance from the tip. The pacemaker device comprises a communication interface for transmitting a communication signal comprising information relating to the mapping signal vector from the pacemaker device to an external device outside of the human body. In this embodiment, the first mapping electrode and the second mapping electrode are part of the leadless pacemaker device. The first mapping electrode and the second mapping electrode may, during actual operation once implanted, also be used for emitting a pacing signal for stimulating the HIS bundle, such that in a mapping mode by means of the first mapping electrode and the second mapping electrode an electrogram is picked up which resembles what the leadless pacemaker electrically sees during actual operation.

If the first mapping electrode and the second mapping electrode are arranged on the leadless pacemaker, care must be taken that signals can be picked up by the first mapping electrode and the second mapping electrode during placement of the leadless pacemaker device by means of the catheter device. For this, the leadless pacemaker device, for mapping, may partially be deployed from the catheter device by pulling back the catheter device to expose the first mapping electrode and the second mapping electrode of the pacemaker device.

In another embodiment, the catheter device may comprise at least one window exposing for example the second mapping electrode, in which case the leadless pacemaker device does not necessarily need to be partially deployed for mapping. This may ease the placement of the pacemaker device, as during placement the pacemaker device is not sticking out substantially from the catheter device, but can be received within the catheter device.

In another embodiment, the first mapping electrode and the second mapping electrode are arranged on the catheter device. The first mapping electrode herein may be placed immediately at the distal end of the catheter device, wherein the second mapping electrode may be placed at a distance from the distal end. In one embodiment, the distance between the first mapping electrode and the second mapping electrode herein matches the distance between a first electrode and a second electrode arranged on the leadless pacemaker device for generating and emitting a pacing signal for stimulating the HIS bundle. In this way it can be achieved that during placement an electrogram from the catheter device is sensed which matches what the leadless pacemaker device sees during actual operation in an implanted state.

In one embodiment, multiple first mapping electrodes and/or second mapping electrodes are placed on the catheter device, for example spaced with respect to each other along a circumferential direction about the catheter device, for example such that neighboring mapping electrodes are spaced apart by an angle of 90°. In this way multiple mapping vectors can be sensed, allowing to derive information with respect to the direction of signal reception during mapping.

In addition or alternatively, multiple ring mapping electrodes can be used to sense a nearfield response and a farfield response, allowing to obtain further information from other regions of the heart to derive mapping information.

The mapping electrodes placed on the catheter device may, by suitable electrical circuit conductors running along the catheter device, be connected with an external monitoring circuitry.

In one embodiment, one of the mapping electrodes of the catheter device may also be used as a fluoro marker to provide additional visibility during implant.

In another embodiment, the first mapping electrode and the second mapping electrode may be placed on a mapping wire received within the catheter device, for example in the lumen or in a side lumen separate from the main lumen. Because the catheter device does not need to comprise additional mapping electrodes in this case, the construction of the catheter device is less complex. The mapping wire may be angled to traverse towards the center of the delivery catheter at the distal end of the catheter device, allowing to sense a mapping signal close to the location at which a pacing electrode of the leadless pacemaker device will be placed after implant.

The mapping electrodes placed on the mapping wire may be connected, by means of suitable electric circuit conductors running along the mapping wire, with an external monitoring circuitry.

In another embodiment, a conventional mapping catheter passing through a main lumen of the catheter device may be used.

In another aspect, a method for placing a leadless pacemaker device using a delivery system as described above is provided. The method comprises: in a mapping mode, sensing, using the first mapping electrode and the second mapping electrode arranged in the vicinity of the distal end of the catheter device, a first mapping signal vector in between the first mapping electrode and the second mapping electrode, the mapping signal vector representing an electrogram of cardiac activity.

Other features which are considered as characteristic for the invention are set forth in the appended claims.

Although the invention is illustrated and described herein as embodied in a leadless cardiac pacemaker device configured to provide HIS bundle pacing, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 15 is a table illustrating an atrial detection algorithm; and

FIG. 16 is a table illustrating a ventricular detection algorithm.

DETAILED DESCRIPTION OF THE INVENTION

Figure 1:
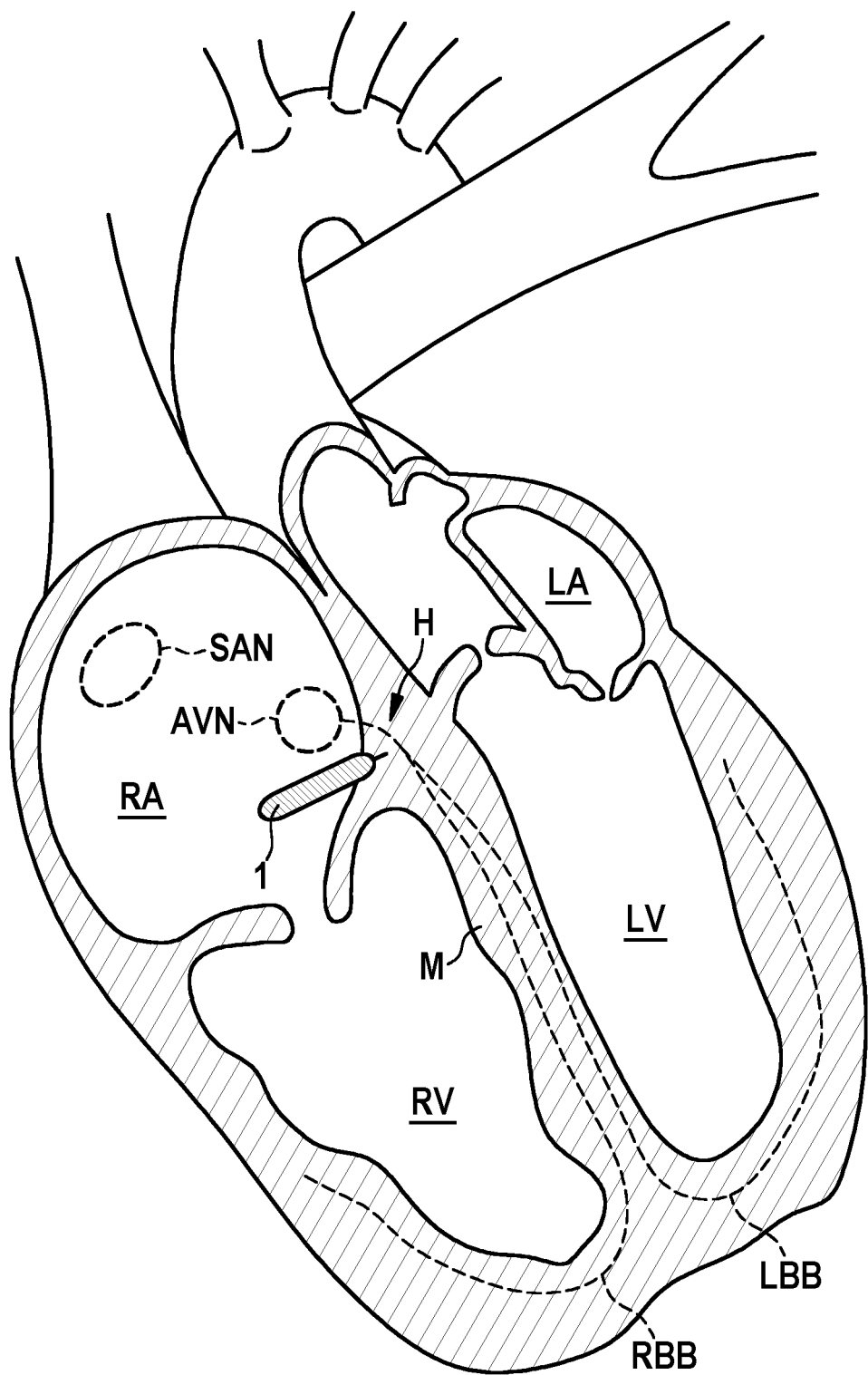
FIG. 1 is a schematic view of a human heart, including a Sinotrial node, an Atrioventricular node, a HIS bundle and a left bundle branch and right bundle branch extending from the HIS bundle.

Subsequently, embodiments of the invention shall be described in detail with reference to the drawings. In the drawings, like reference numerals designate like structural elements.

It is to be noted that the embodiments are not limiting for the invention, but merely represent illustrative examples.

In the instant invention it is proposed to provide a leadless pacemaker device providing for HIS bundle pacing.

Referring now to the figures of the drawings in detail and first, particularly to FIG. 1 thereof, there is shown, in a schematic drawing, a human heart comprising the right atrium RA, the right ventricle RV, the left atrium LA and the left ventricle LV, the so-called sinoatrial node SAN being located in the wall of the right atrium RA. The sinoatrial node SAN being formed by a group of cells having the ability to spontaneously produce an electrical impulse that travels through the heart's electrical conduction system, thus causing the heart to contract in order to pump blood through the heart. The atrioventricular node AVN serves to coordinate electrical conduction in between the atria and the ventricles and is located at the lower back section of the intra-atrial septum near the opening of the coronary sinus. From the atrioventricular node AVN the so-called HIS bundle H is extending, the HIS bundle H being comprised of heart muscle cells specialized for electrical conduction and forming part of the electrical conduction system for transmitting electrical impulses from the atrioventricular node AVN via the so-called right bundle branch RBB around the right ventricle RV and via the left bundle branch LBB around the left ventricle LV.

As electrical impulses from the atrioventricular node AVN are transmitted collectively via the HIS bundle H towards the right bundle branch RBB and the left bundle branch LBB for stimulating the right ventricle RV and the left ventricle LV, HIS bundle pacing has the potential to synchronously pace the right ventricle RV and the left ventricle LV, hence avoiding a lack of synchrony in between the left ventricle RV and the right ventricle RV as it may occur for example in a right ventricular pacing.

Whereas common pacemaker devices providing for an HIS bundle pacing use leads extending from the (subcutaneously implanted) pacemaker device transvenously into the heart, it is proposed within the instant invention to use a leadless pacemaker device 1 for implementation into the right atrium RA to provide for an HIS bundle pacing at the HIS bundle H, as schematically indicated in FIG. 1. By means of such leadless pacemaker device 1, stimulation energy is injected into the right atrial wall at the HIS bundle H in order to provide for a pacing at the HIS bundle H.

In another embodiment, the leadless pacemaker is implanted in the high right ventricular septum in order to pace at or near the HIS from the ventricle (rather than from the atrium). This ventricular implant location may be better for patients with small atriums, and may have some implant stability advantages over atrial placement.

Figure 12:
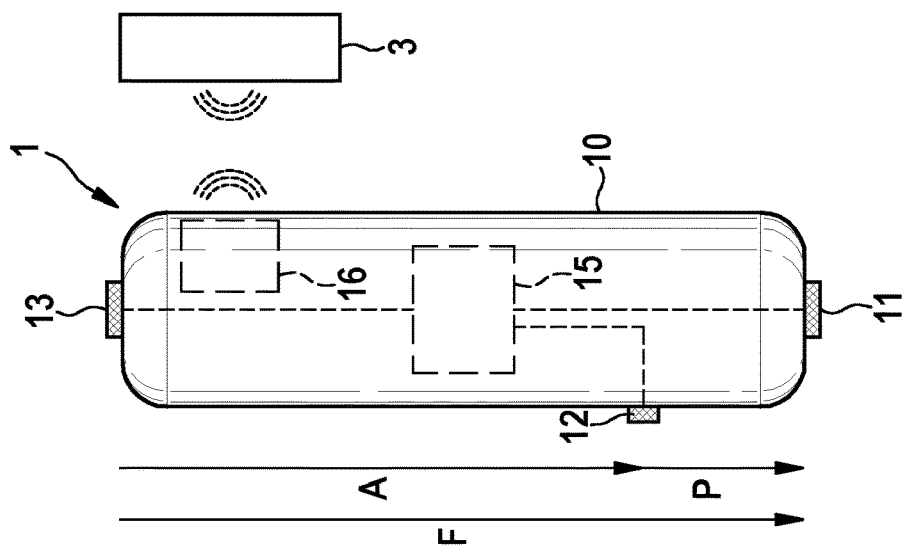
FIG. 12 is a view of a schematic view of \the leadless pacemaker device.

Referring now to FIG. 12, in one embodiment a leadless pacemaker device 1 configured to provide for an HIS bundle pacing comprises a housing 10 enclosing electrical and electronic components for operating the leadless pacemaker device 1. In particular, enclosed within the housing 10 is a processor 15 and a communication interface 16 for communicating with an external device 3, such as a programmer wand, wherein in addition electrical and electronic components such as an energy storage in the shape of a battery are confined in the housing 10. In one embodiment the battery casing itself makes up part of the housing 10. The housing 10 provides for an encapsulation of components received therein, the housing 10 having the shape of, e.g., a cylindrical shaft having a length of for example a few centimeters.

In the embodiment of FIG. 12, the leadless pacemaker device 1 comprises different electrodes 11, 12, 13 serving to emit pacing signals towards the HIS bundle H for providing HIS bundle pacing and to sense electrical signals indicative of cardiac activity, in particular indicative of atrial and ventricular contractions.

A first electrode 11 herein is denoted as pacing electrode and is placed close to the HIS bundle H upon implanting the leadless pacemaker device 1. The first electrode 11 is placed at a tip of the housing 10 and is configured to engage with cardiac tissue in order to come to rest close to the HIS bundle H.

A second electrode 12 serves as a counter electrode for the first electrode 11, a signal vector P arising between the first electrode 11 and the second electrode 12 providing for a pacing vector P for emitting pacing signals towards the HIS bundle H. In addition, the second electrode 12 serves as a sensing electrode for sensing signals, in particular relating to atrial and ventricular contractions. The second electrode 12 is placed at a distance from the first electrode 11 and for example has the shape of a ring. The second electrode 12 is for example placed at a distance of about 1 cm from the tip of the housing 10 at which the first electrode 11 is placed.

The leadless pacemaker device 1, in the embodiment of FIG. 12, in addition comprises a third electrode 13 placed at a far end of the housing 10, the third electrode 13 serving as a sensing electrode for sensing signals indicative of cardiac activity. In particular, a signal vector A arises between the third electrode 13 and the second electrode 12, the signal vector A picking up signals being indicative for example of atrial contractions. In addition, a signal vector F arises between the third electrode 13 and the first electrode 11, the signal vector F being indicative for example of ventricular contractions. The signal vector F also is denoted as farfield vector.

The electrodes 11, 12, 13 are in operative connection with the processor 15, the processor 15 being configured to cause the first electrode 11 and the second electrode 12 to emit a pacing signal for stimulating the HIS bundle H for an HIS bundle pacing. The processor 15 furthermore is configured to process signals received via the electrodes 11, 12, 13 to provide for a sensing of cardiac activity, in particular atrial and ventricular contractions. By being able to record both atrial and ventricular activity, the leadless pacemaker device 1 can provide AV synchronous pacing.

One challenge in implanting a leadless pacemaker device 1 at the HIS bundle H is to provide for a mapping in order to correctly place the leadless pacemaker device 1 with its pacing electrode 11 in close proximity to the HIS bundle H. Within a mapping technique, the HIS bundle H shall be located by electrophysiological measurements in order to ensure that the leadless pacemaker device 1 is correctly placed at the HIS bundle H in order to provide for an effective HIS bundle pacing.

Figure 2:
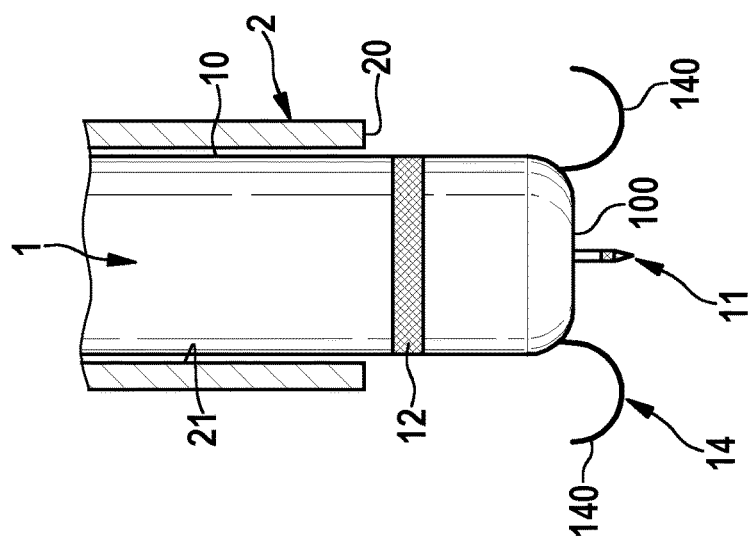
FIG. 2 is a view of an embodiment of a leadless pacemaker device received within a catheter device, partially deployed for mapping during placement according to the invention.

Referring now to FIG. 2, in one embodiment the leadless pacemaker device 1 in a mapping mode is configured to sense a real-time electrogram in between the first electrode 11 and the second electrode 12 during placement of the leadless pacemaker device 1 in the human heart. For placement, the leadless pacemaker device 1 is received within a lumen of a catheter device 2 forming part of a delivery system, the leadless pacemaker device 1 being received at a distal end 20 of the catheter device 2 in order to deliver the leadless pacemaker device 1 into the human heart.

For mapping, the leadless pacemaker device 1 in one embodiment is partially deployed from the distal end 20 of the catheter device 2, as illustrated in FIG. 2, such that the first electrode 11 and the second electrode 12 are exposed for sensing electrical cardiac signals in order to record a real-time electrogram. By means of the communication interface 16 as illustrated in FIG. 12 a recorded electrogram can be transferred to an external device 3 such as a programmer wand, such that the electrogram may be monitored and assessed in order to determine whether the HIS bundle H has been reached.

In the embodiment of FIG. 2, the first electrode 11 is placed on a pin at a tip 100 of the housing 10 of the leadless pacemaker device 1. Upon implant, the first electrode 11 is inserted into cardiac tissue, in particular the right atrial wall (or in one embodiment, the high RV septum), such that via the first electrode 11 during actual pacing operation stimulation after implant energy may be transmitted towards the HIS bundle H for HIS bundle pacing. Because, in the mapping mode, sensing signals are received via the first electrode 11 and the second electrode 12, the leadless pacemaker device 1 during placement sees, in terms of electrical coupling to the HIS bundle H, what the device 1 will see after implant during actual pacing operation. If during placement a HIS bundle capture is picked up via the first electrode 11 and the second electrode 12, it is ensured that also during actual pacing operation after implant stimulation energy can effectively be injected into the HIS bundle H.

As the electrogram recorded via the first electrode 11 and the second electrode 12 during placement is communicated towards the outside via the communication interface 16, the electrogram may be monitored and may be assessed in order to evaluate whether correct placement has been achieved. The communication interface 16 herein may be configured to provide for a communication by inductive coupling, by MICS, by a BLE, by acoustic communication, or by E-field communication. Signals indicative of a recorded real-time electrogram hence are transmitted using telemetry from the leadless pacemaker device 1 towards an external device 3 outside of the human body in the mapping mode.

Figure 3:
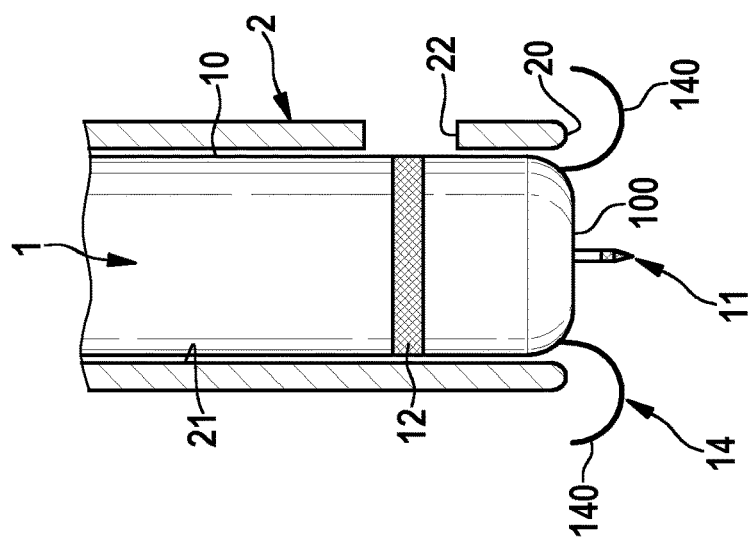
FIG. 3 is a view of another embodiment of the leadless pacemaker device received within the catheter device.

Referring now to FIG. 3, in another embodiment the catheter device 2 comprises a window 22 in the region at which the second electrode 12 is placed when the leadless pacemaker device 1 is received within the catheter device 2 for placement in the human heart. In this embodiment, no partial deployment of the leadless pacemaker device 1 for placement is necessary, but the leadless pacemaker device 1 can remain seated in the catheter device 2, hence potentially easing the placement of the leadless pacemaker device 1 in the right atrium RA as the leadless pacemaker device 1 does not stick out from the catheter device 2 during placement. By means of the window 22 the second electrode 12 is exposed in order to sense signals, wherein in addition the electrode 11 at the tip 100 of the housing 10 of the leadless pacemaker device 1 is exposed at the distal end 20 of the catheter device 2 such that a sensing vector can be picked up in between the electrodes 11, 12 for mapping.

Figure 4:
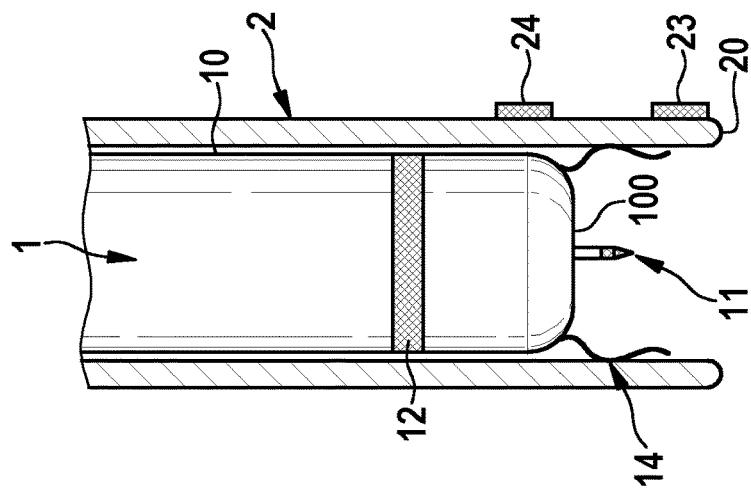
FIG. 4 is a view of yet another embodiment of the leadless pacemaker device received within the catheter device during placement.

Referring now to FIG. 4, in another embodiment mapping electrodes 23, 24 are arranged on the catheter device 2, a first mapping electrode 23 for example being placed immediately at a distal end 20 of the catheter device 2, and a second mapping electrode 24 being placed at a distance from the distal end 20 and hence from the first mapping electrode 23. The shape, size and distance of the electrodes 23, 24 herein, preferably, resembles the shape, size and distance of the electrodes 11, 12 of the leadless pacemaker device 1, such that an electrogram picked up via the mapping electrodes 23, 24 during placement resembles what the electrodes 11, 12 of the leadless pace maker device 1 will see during actual pacing operation after implant.

Figure 5:
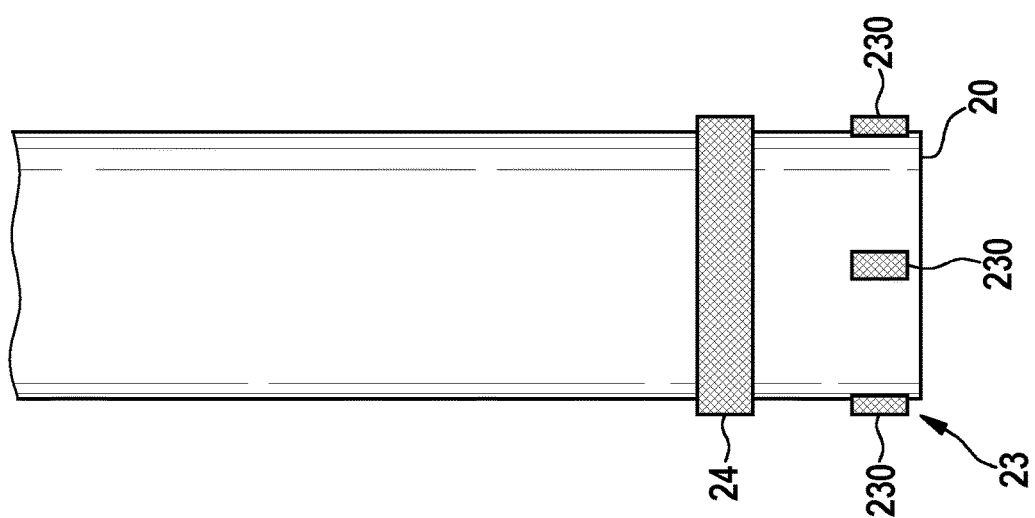
FIG. 5 is a schematic view of the catheter device having electrodes at a tip.

Referring now to FIG. 5, different shapes and arrangements of the electrodes 23, 24 on the catheter device 2 are conceivable. For example, multiple first mapping electrode elements 230 may be circumferentially spaced with respect to each other at the distal end 20 of the catheter device 2, for example by an angle of 90° between neighboring electrode elements 230. The second mapping electrode 24 may for example have the shape of a ring circumferentially extending about the catheter device 2, wherein it is also conceivable that multiple second electrode elements making up the electrode 24 are present. By using multiple electrode elements it may be possible to pick up different mapping signal vectors, allowing for example to derive information indicative of a direction of signal reception, hence further facilitating the placement and mapping for arranging the leadless pacemaker device 1 at the HIS bundle H.

Figure 6:
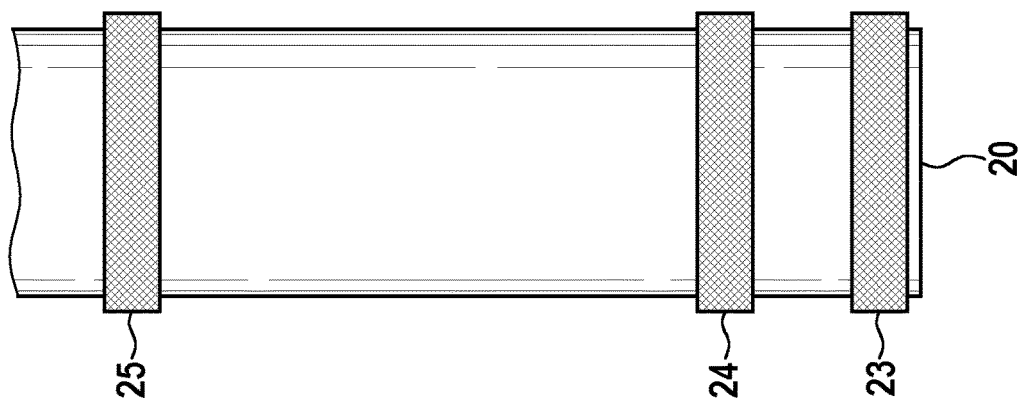
FIG. 6 is a schematic view of another embodiment of the catheter device.

Referring now to FIG. 6, it also is conceivable to provide multiple electrodes 23, 24, 25 on the catheter device 2, the electrodes 23, 24, 25 being axially spaced apart and for example being shaped as rings extending about the catheter device 2. By means of such ring electrodes 23, 24, 25 nearfield and farfield vectors may be picked up, hence allowing to detect both a nearfield response and a farfield response.

In one embodiment, one or multiple of the electrodes 23, 24, 25 of the catheter device 2 are also used as fluoro markers for additional visibility during implant.

Figure 7:
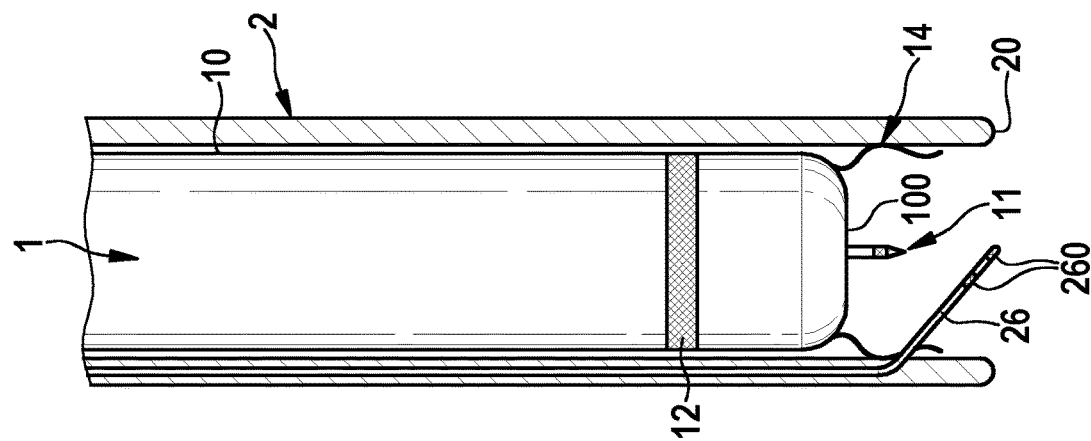
FIG. 7 is a view of an embodiment of the leadless pacemaker device received in the catheter device, a mapping wire being received within the catheter device for mapping.

Referring now to FIG. 7, in another embodiment a mapping wire 26 is received in a side lumen of the catheter device 2 separate from the main lumen. The mapping wire 26 is angled towards the center of the catheter device 2 at the distal end 20, the mapping wire 26 carrying mapping electrodes 260 at its angled end, the electrodes 260 allowing to sense a mapping signal during implant of the leadless pacemaker device 1.

In another embodiment, a regular mapping catheter received in the main lumen is used for mapping when implanting the leadless pacemaker device 1.

The leadless pacemaker device 1, in one embodiment, is to be placed in the right atrium RA, as this schematically as illustrated in FIG. 1. For the implant, the leadless pacemaker device 1 is to be fixed to the atrial wall, hence requiring a fixation device providing for a reliable and permanent fixture of the leadless pacemaker device 1 in the right atrium RA.

As the atrial wall of the right atrium RA typically is comparatively thin and more delicate than for example the ventricular wall, a fixation device is to be configured such that a penetration of the atrial wall and a damage of the nerve structure near the HIS bundle H is prevented.

Figure 8:
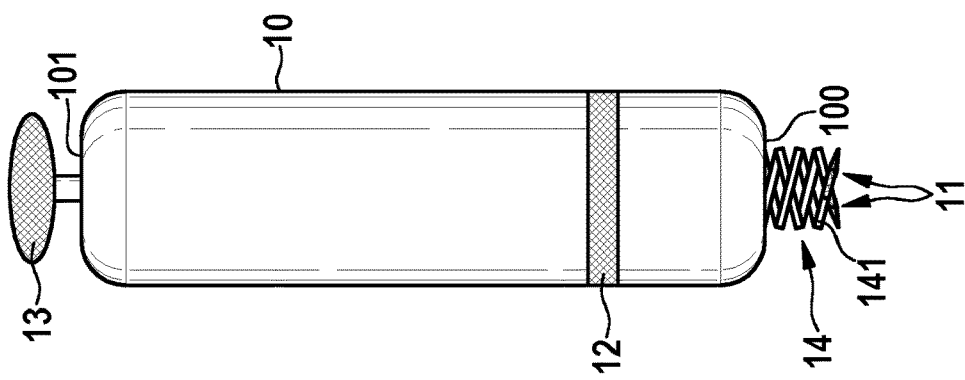
FIG. 8 is a view of an embodiment of the leadless pacemaker device.

Referring now to FIG. 8, in one embodiment, a fixation device 14 at the tip 100 of the housing 10 of the leadless pacemaker device 1 comprises a multiplicity of curved fixation elements 140 being formed by wires in the shape of nitinol tines, the fixation elements 140 having for example a radius of curvature smaller than 1.5 mm in order to ensure that the fixation elements 140 do not penetrate deeply into the cardiac wall.

In the embodiment of FIG. 8, the first electrode 11 is placed on a pin 110, the pin 110 engaging the atrial wall at the HIS bundle H during implant such that the electrode 11 comes to rest in close proximity to the HIS bundle H. The pin 110 has a pointed shape and has a length of for example in between 1 mm and 3 mm, for example approximately 2 mm.

The second electrode 12, in the embodiment of FIG. 8, has a ring shape and circumferentially extends about the housing 10 of the leadless pacemaker device 1, the housing 10 having a generally cylindrical shape. A third electrode 13 is placed at a far end 101 of the housing 10 opposite the first electrode 11.

Figure 9:
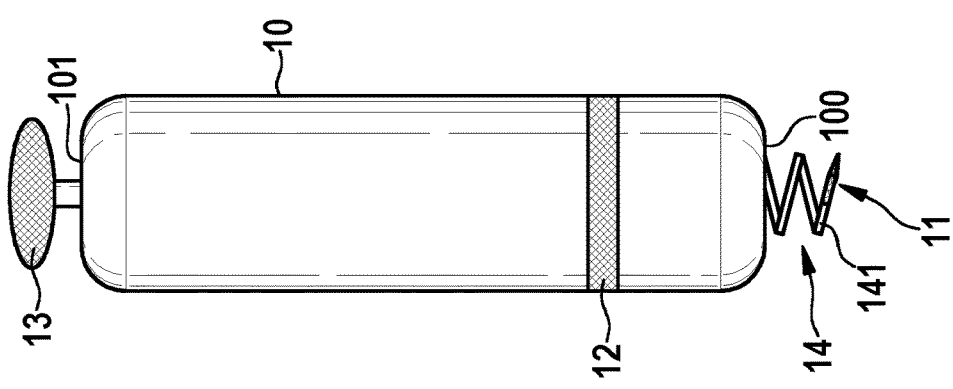
FIG. 9 is a view of another embodiment of the leadless pacemaker device.

Referring now to FIG. 9, in one embodiment multiple (here: three) first electrodes 11 are placed on multiple pins 110 at the tip 100 of the housing 10 of the leadless pacemaker device 1. During implant the pins 110 engage with cardiac tissue, the processor device 15 for example being configured to select one or a group of the first electrodes 11. In this way an electrode of the first electrodes 11 may be chosen which is arranged closest to the HIS bundle H and hence has the strongest electrical coupling with the HIS bundle H. Because multiple first electrodes 11 are available for selection, a potential need for repositioning the leadless pacemaker device 1 during implant at least can be reduced.

Figure 10:
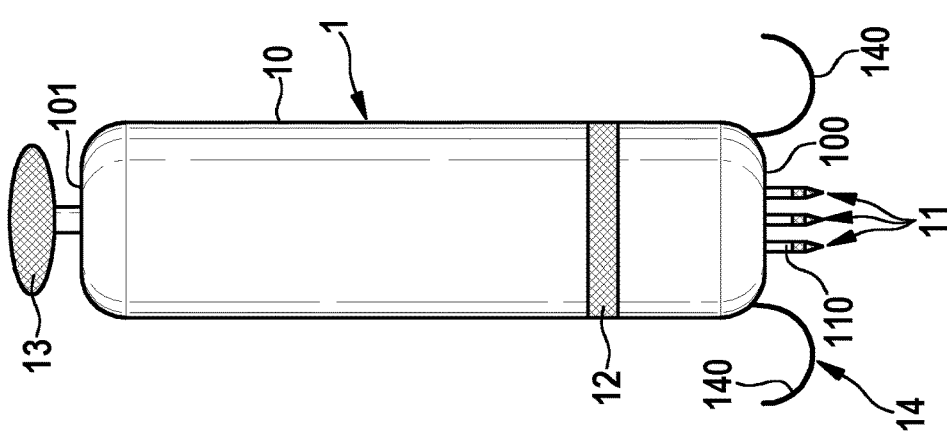
FIG. 10 is a view of yet another embodiment of the leadless pacemaker device.
Figure 11:
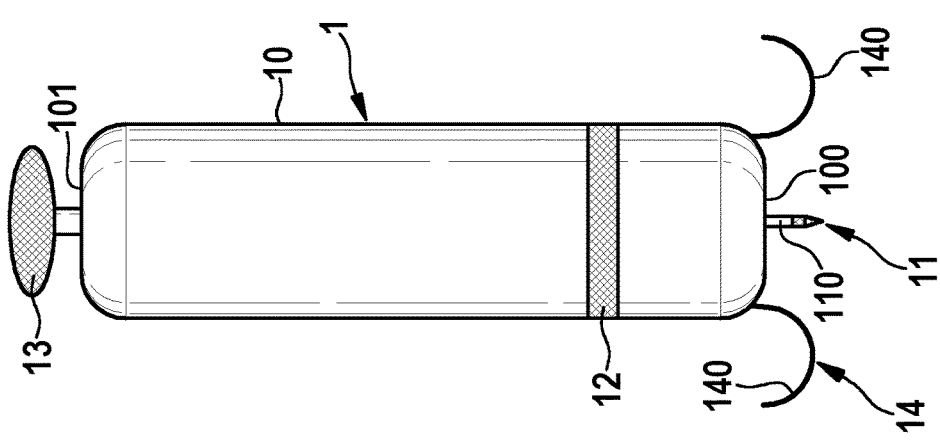
FIG. 11 is a view of yet another embodiment of the leadless pacemaker device.

Referring now to FIG. 10, in one embodiment the fixation device 14 comprises a screw anchor 141, the screw anchor 141 serving to screw into cardiac tissue in order to fix the leadless pacemaker device 1 within the right atrium RA. The first electrode 11 herein is placed at a tip of the screw anchor 141, such that by engagement of the screw anchor 141 in cardiac tissue the electrode 11 comes to rest in close proximity to the HIS bundle H. The screw anchor 141 may for example have a diameter equal to or smaller than 2 mm in order to minimize the risk for damaging the nerve structure near the HIS bundle H during implant.

In one embodiment, the screw anchor 141 may comprise multiple arms to form a double or triple helix, each arm for example carrying a first electrode 11 such that—similar to the embodiment of FIG. 9—the processor 15 may be configured to select one or a group of the electrodes 11 for operation in order to select such electrode 11 which is closest and best coupled to the HIS bundle H. In another embodiment a single screw anchor 141 contains multiple electrodes along its length, each individually selectable by the processor 15.

In the embodiments of FIGS. 8 to 11, the pin 110 respectively the screw anchor 141 may comprise an electrically insulating coating, such that only the electrode 11 is electrically exposed. This may help to reduce the risk of accidental atrial capture.

During an actual pacing operation, the processor 15 may switch between a sensing mode and a stimulation mode in order to sense signals indicative of cardiac activity and to generate pacing signals for stimulating the HIS bundle H in an alternating fashion.

Figure 13:
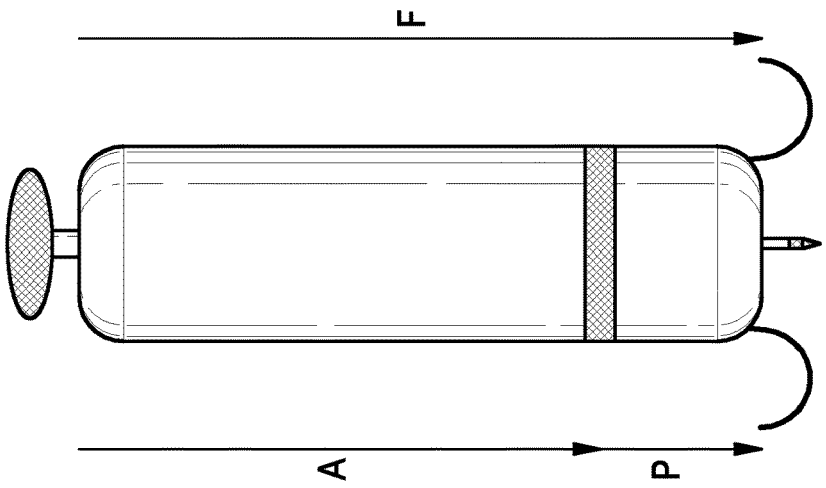
FIG. 13 is a schematic view of the leadless pacemaker device, indicating signal vectors sensed between different electrodes of the leadless pacemaker device.

In particular, in a first phase of the cardiac cycle, atrial contractions may be sensed for example by a signal vector A in between the second electrode 12 and the third electrode 13 as illustrated in FIGS. 12 and 13. Following an atrial capture, in a second phase of the cardiac cycle a pacing signal is emitted by means of a pacing vector P in between the first electrode 11 and the second electrode 12 in order to inject stimulation energy at the HIS bundle H, the pacing signal being injected with adequate timing after the atrial capture in order to provide for atrial to ventricular (A to V) synchrony. After injection of the pacing signal, the processor 15 may switch back into a sensing mode in order to sense an evoked response by picking up ventricular contractions via the farfield vector F in between the first electrode 11 and the third electrode 13.

Different sensing algorithms for obtaining atrial and ventricular captures and different pacing algorithms for capturing the HIS bundle may be used. An atrial sensing algorithm may for example be similar to an atrial DX algorithm. For sensing ventricular signals an increased amplification may be required as for the leadless pacemaker 1 ventricular contractions occur in the farfield and hence require a stronger amplification.

Figure 14:
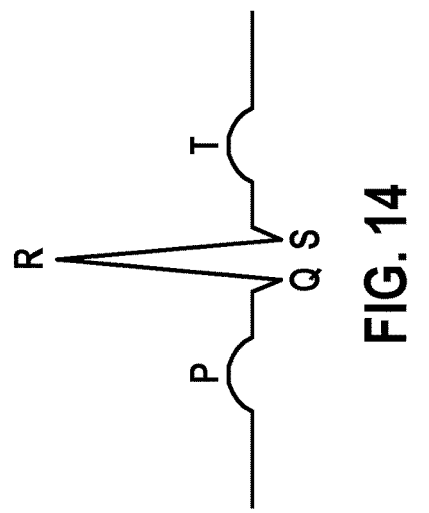
FIG. 14 is an illustration of an electrocardiogram signal.

In order to provide for a pacing at the HIS bundle H, an automated capture algorithm may be used. Within the capture algorithm the QRS waveform in the ECG as illustrated in FIG. 14 may be examined, a short QRS waveform indicating a capture of the HIS conduction pathway without recruitment of surrounding cardiac tissue. An automated capture algorithm herein may include a periodic search, for example once per hour, by increasing and decreasing the pacing threshold and by monitoring a QRS response. The processor 15 may then for example be configured to choose the pacing amplitude having the smallest QRS width, wherein for the further pacing operation the pacing amplitude determined in this way may be used.

An embodiment of an atrial sensing algorithm is illustrated in the table of FIG. 15.

In case atrial activity has not been sensed for an extended period of time the processor 15 may be configured to attempt to synchronize with atrial activity that is present but not detected. For this, the timing of the pacing may be adapted. For example, if a previous intrinsic distance between ventricular signals (V-V) has been X milliseconds, the next pacing signal should be injected earlier than the intrinsic V-V of the previous cycle by some value, for example by 10% or 10 ms (third row in the table of FIG. 15). This causes a shortening of the A/V. When in this mode, the processor 15 should be configured to periodically check the intrinsic V-V by allowing intrinsic conduction, for example once in a minute or once every 5 minutes.

In FIG. 16, an embodiment of a ventricular sensing algorithm to capture an evoked response is illustrated.

Since the leadless pacemaker device 1 is placed in the right atrium RA, it can sense the atrial signal with its atrial dipole in between the second electrode 12 and the third electrode 13. If the device should detect that the patient is in a state of atrial fibrillation (AF), the processor is configured to drive the ventricle by pacing the AF rate as set by the clinician. Driving the ventricle during the state of AF is desirable because it will continue to provide LV-RV synchrony, which may not be present in intrinsic beats.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

When reading the claim language, the following definitions apply. When the claim language recites A and/or B it means A alone, B alone or A and B. When the claim language recites at least one of A and B it means A alone, B alone or A and B. When the claim language recites at least one of A or B it means A alone, B alone or A and B.

LIST OF REFERENCE NUMERALS

1 Leadless pacemaker device
10 Housing
100 Tip
101 Far end
11 First electrode (pacing electrode)
110 Pin
12 Second electrode (pacing ring)
13 Third electrode
14 Fixation device
140 Fixation element (wire)
141 Fixation element (screw)
15 Processor
16 Communication interface
2 Catheter device
20 Distal end
22 Window
23 Electrode
230 Electrode element
24 Electrode
25 Electrode
26 Mapping wire
260 Electrodes
3 External device (programmer wand)
A Atrial vector
AVN Atrioventricular node
F Farfield vector
H HIS bundle
LA Left atrium LBB Left bundle branch
LV Left ventricle
M Intra-cardiac tissue (myocardium)
P Pacing vector
RA Right atrium
RBB Right bundle branch
RV Right ventricle
SAN Sinoatrial node

The invention claimed is:

1. A leadless cardiac pacemaker device configured to provide conduction system pacing or HIS bundle pacing, the leadless cardiac pacemaker device comprising:
a housing having a tip and a far end opposite said tip;
a first electrode disposed on said housing in an area of said tip, said first electrode configured to engage with intra-cardiac tissue;
a second electrode disposed on said housing at a distance from said tip of said housing;
a third electrode disposed on said housing in an area in the vicinity of said far end; and
a processor enclosed in said housing and operatively connected to said first electrode and to said second electrode, wherein said processor is configured to process a reception signal received by at least one of said first electrode and said second electrode and to generate a pacing signal to be emitted using at least one of said first electrode and said second electrode;
wherein said processor is configured to process, as the reception signal, at least one of a second signal vector sensed between said first electrode and said third electrode and a third signal vector sensed between said second electrode and said third electrode; and
wherein said processor is configured to alternate between processing at least one of the second signal vector sensed between said first electrode and said third electrode and the third signal vector sensed between said second electrode and said third electrode and generating the pacing signal to be emitted using at least one of said first electrode and said second electrode.

2. The leadless cardiac pacemaker device according to claim 1, further comprising a fixation device having at least one fixation element disposed at said tip of said housing for fixing the leadless cardiac pacemaker device to the intra-cardiac tissue.

3. The leadless cardiac pacemaker device according to claim 1, wherein:
said first electrode is one of a plurality of first electrodes disposed on said housing in the area of said tip; and
said processor is configured to select at least one of said plurality of first electrodes for at least one of receiving the reception signal and emitting the pacing signal.

4. The leadless cardiac pacemaker device according to claim 1,
wherein said second electrode is formed by an electrode ring circumferentially extending about said housing.

5. The leadless cardiac pacemaker device according to claim 1, further comprising a communication interface for transmitting a communication signal containing information relating to the first signal vector from the leadless cardiac pacemaker device to an external device outside of a human body.

6. The leadless cardiac pacemaker device according to claim 1, wherein said processor is configured to process at least one of the second signal vector to detect atrial activity, and the third signal vector to detect ventricular activity.

* * * * *